US006433121B1

(12) United States Patent
Petrovic et al.

(10) Patent No.: US 6,433,121 B1
(45) Date of Patent: Aug. 13, 2002

(54) METHOD OF MAKING NATURAL OIL-BASED POLYOLS AND POLYURETHANES THEREFROM

(75) Inventors: Zoran Petrovic, Pittsburgh; Ivan Javni, Pittsburg; Andrew Guo, Pittsburg; Wei Zhang, Pittsburg, all of KS (US)

(73) Assignee: Pittsburg State University, Pittsburg, KS (US)

( * ) Notice: Subject to any disclaimer, the term of this patent is extended or adjusted under 35 U.S.C. 154(b) by 120 days.

(21) Appl. No.: 09/612,716

(22) Filed: Jul. 10, 2000

Related U.S. Application Data

(63) Continuation-in-part of application No. 09/187,992, filed on Nov. 6, 1998, now Pat. No. 6,107,433.

(51) Int. Cl.[7] .............................. C08J 3/00; C08K 3/20; C08L 75/00; C08G 83/00; C09F 1/00
(52) U.S. Cl. ........................ 528/1; 527/600; 530/200; 530/205
(58) Field of Search .................. 527/600; 530/200, 530/205; 528/1

(56) References Cited

U.S. PATENT DOCUMENTS

| 3,454,539 A | * | 7/1969 | Greenlee ..................... 260/79 |
|---|---|---|---|
| 4,508,853 A | | 4/1985 | Kluth et al. |
| 4,546,120 A | | 10/1985 | Peerman et al. |
| 4,551,517 A | | 11/1985 | Herold et al. |
| 4,742,087 A | | 5/1988 | Kluth et al. |
| 4,826,944 A | | 5/1989 | Hoefer et al. |
| 4,886,893 A | | 12/1989 | Jeffert et al. |
| 5,026,881 A | | 6/1991 | Gruber |
| 5,266,714 A | | 11/1993 | Stoll et al. |
| 5,302,626 A | | 4/1994 | Hoefer et al. |

FOREIGN PATENT DOCUMENTS

| DE | 39 43 080 | 7/1991 |
|---|---|---|
| DE | 41 15 146 | 11/1992 |
| DE | 41 28 649 | 3/1993 |

OTHER PUBLICATIONS

Scholnick et al., "Urethane Foams from Animal Fats. IV. Rigid Foams from Epoxidized Glycerides," *Journal of the American Oil Chemists' Society*, vol. 45, pp. 76–77, 1968.

* cited by examiner

*Primary Examiner*—Patrick D. Niland
(74) *Attorney, Agent, or Firm*—Stinson Morrison Hecker LLP

(57) ABSTRACT

A method for making natural oil-based polyols directly from vegetable or animal oil using a consecutive two-step process involving epoxidation and hydroxylation is provided. Specifically, this process comprises adding a peroxyacid to a natural oil wherein said natural oil and said peroxyacid react to form an epoxidized natural oil and adding said epoxidized natural oil to a mixture of an alcohol, water, and a fluoboric acid catalyst. The catalytic amount of fluoboric acid is less than about 0.5% by weight of the entire reaction mixture, and the amount of water is about 10 to 30% by weight of the entire mixture. The epoxidized natural oil undergoes hydroxylation and forms a natural oil-based polyol. The present invention further includes a method for making natural oil-based polyols from epoxidized oil by hydroylating the epoxidized oil in the presence of fluoboric acid, alcohol and water in the amounts discussed above.

The natural oil-based polyols created by this method may be reacted with isocyanates so as to form polyurethanes, which is another embodiment of the present invention. Alternatively, fillers such as silica may be combined with these natural oil-based polyols before they are reacted with isocyanates to form polyurethanes. In still another embodiment of the present invention, polyurethanes made from natural oil-based polyols may be used to form electroinsulating casting resins for use in electrical applications.

14 Claims, No Drawings

METHOD OF MAKING NATURAL OIL-BASED POLYOLS AND POLYURETHANES THEREFROM

CROSS REFERENCE TO RELATED APPLICATIONS

This application is a continuation-in-part of U.S. application Ser. No. 09/187,992, filed Nov. 6, 1998 now U.S. Pat. No. 6,107,433.

STATEMENT REGARDING FEDERALLY-SPONSORED RESEARCH OR DEVELOPMENT

Not Applicable.

BACKGROUND OF THE INVENTION

The present invention relates to a method for making natural oil-based polyols. Still further, the present invention includes using natural oil-based polyols to produce polyurethane resins for use as casting compounds for electrical applications.

Polyols may be produced from petroleum. However, there has been an active trend in recent years to use renewable resources, such as vegetable and animal oils. Vegetable and animal oil molecules must be chemically transformed in order to introduce hydroxyl groups. For instance, A soybean oil does not contain any hydroxyl groups but has on average about 4.6 double bonds per molecule. The unsaturated portions of the vegetable or animal oil molecule can be converted to hydroxyl groups. However, many reactions for preparing polyols from various natural oils are not very selective. By-products, in addition to alcohol groups, are created during the transformation. Furthermore, many conventional methods of preparing polyols from natural oils do not produce polyols having a significant content of hydroxyl groups. Still further, many available methods of preparing polyols from natural oils do not produce products having a desirable viscosity. Greases or waxes of ten result as a consequence of such chemical transformations.

Conventionally, cast electrical components such as dry voltage transformers and insulators are formed from epoxy resins. Epoxy resins are rather expensive to use. Still further, epoxy resins are not easy to handle at low temperatures and have poor elasticity. Polyurethane resins prepared with castor oil have also been produced. However, these resins tend to be rubbery and thus undesirable for certain casting applications. Still further, castor oil-based polyurethanes have some limitations due to their higher price and environmental problems related to their by-products.

In order to overcome the deficiencies found with conventional processes for making natural oil-based polyols, a method for making natural oil-based polyols from vegetable or animal oil or epoxidized vegetable or animal oil is needed for a variety of applications including preparation of, through polyurethane chemistry, a resin for use as an electroinsulating casting compound, which is another embodiment of the present invention. Still further, this method of making natural oil-based polyols should avoid substantial side reactions, such as esterification, cyclization, polymerization, crosslinking, and other undesirable reactions, and should produce polyols having a high hydroxyl content and a desirable viscosity.

SUMMARY OF THE INVENTION

According to the present invention, a method for making natural oil-based polyols directly from vegetable or animal oil using a consecutive two-step process involving epoxidation and hydroxylation is provided. Specifically, this process comprises adding a peroxyacid to a natural oil wherein said natural oil and said peroxyacid react to form an epoxidized natural oil and adding said epoxidized natural oil to a mixture of an alcohol, water, and a fluoboric acid catalyst. The catalytic amount of fluoboric acid is less than about 0.5% by weight of the entire reaction mixture, and the amount of water is about 10 to 30% by weight of the entire mixture. The epoxidized natural oil undergoes hydroxylation and forms a natural oil-based polyol. The present invention further includes a method for making natural oil-based polyols from epoxidized oil by hydroylating the epoxidized oil in the presence of fluoboric acid, alcohol and water in the amounts discussed above.

The natural oil-based polyols created by this method may be reacted with isocyanates so as to form polyurethanes, which is another embodiment of the present invention. Alternatively, fillers such as silica may be combined with these natural oil-based polyols before they are reacted with isocyanates to form polyurethanes. In still another embodiment of the present invention, polyurethanes made from natural oil-based polyols may be used to form electroinsulating casting resins for use in electrical applications.

Additional objects, advantages and novel features of the invention will be set forth in part in the description which follows, and in part will become apparent to those skilled in the art upon examination of the following, or may be learned from practice of the invention. The objects and advantages of the invention may be realized and attained by means of the instrumentalities and combinations particularly pointed out in the appended claims.

DETAILED DESCRIPTION OF THE PREFERRED EMBODIMENT

The method of the present invention involves making natural oil-based polyols by converting each of the double bonds of the natural oil molecule into a hydroxyl group. This method takes place at approximately atmospheric pressure.

The process of the present invention involves epoxidation and subsequent hydroxylation of a natural oil so as to make a polyol. More specifically, the process of the present invention includes adding a peroxyacid in a solvent to a vegetable or animal oil wherein the oil and the peroxyacid react to form an epoxidized oil, and adding said epoxidized oil, which is in the solvent, to a mixture of an alcohol, water, and a catalytic amount of fluoboric acid so as to form a natural oil-based polyol. These are consecutive, non-stop steps. The reaction is not stopped after the epoxidized natural oil forms so as to purify the intermediate product.

Another embodiment of the present invention is a method of making polyols from epoxidized natural oil by the second step of the process outlined above. This second step provides a fast conversion of an epoxidized oil to a polyol. Epoxidized natural oils, the starting component of this second step, can be obtained from Ferro Corporation, C. P. Hall, Ashland Chemicals or Union Carbide or made from natural oil, as discussed above. Preferably, the epoxidized natural oil used in the method of the present invention has an epoxide content between 6–7% by mole epoxy groups per mole of epoxidized natural oil, and it has about 90 to 95% of the double bonds in the natural oil epoxidized. In other terms, preferably, each epoxidized natural oil molecule has about 2–6 epoxy groups. In still other terms, preferably, the epoxidized natural oil used has an epoxide content of 2–8 weight %.

Any vegetable or animal oil may be used in this process. Examples of vegetable and animal oils that may be used include, but are not limited to, soybean oil, safflower oil, linseed oil, corn oil, sunflower oil, olive oil, canola oil, sesame oil, cottonseed oil, palm oil, rapeseed oil, tung oil, fish oil, or a blend of any of these oils. Alternatively, any partially hydrogenated or epoxidized natural oil or genetically modified natural oil can be used to obtain the desired hydroxyl content. Examples of such oils include, but are not limited to, high oleic safflower oil, high oleic soybean oil, high oleic peanut oil, high oleic sunflower oil (NuSun sunflower oil) and high erucic rapeseed oil (Crumbe oil). The iodine values of these natural oils range from about 40 to 220 and more preferably from about 80 to 180. When natural oils having lower iodine values are used to make natural oil-based polyols, polyols with lower hydroxyl numbers and thus lower viscosities are created.

Any peroxyacid may be used in the epoxidation reaction. Examples of peroxyacids that may be used include, but are not limited to, peroxyformic acid, peroxyacetic acid, trifluoroperoxyacetic acid, benzyloxyperoxyformic acid, 3,5-dinitroperoxybenzoic acid, m-chloroperoxybenzoic acid, or any combination of these peroxyacids. The peroxyacids may be formed in-situ by reacting a hydroperoxide with the corresponding acid, such as formic or acetic acid. Examples of hydroperoxides that may be used include, but are not limited to, hydrogen peroxide, tert-butylhydroperoxide, triphenylsilylhydroperoxide, cumylhydroperoxide, or any combination of these hydroperoxides. Preferably, the peroxyacid is in a solvent such as acetic acid, formic acid, or chloroform.

Fluoboric acid is used as the acid catalyst in the hydroxylation step. Using fluoboric acid as a catalyst in this hydroxylation reaction works better than using other inorganic acids suggested by the prior art. Specifically, by using fluoboric acid, the reaction time is shorter, the reactivity is higher, and the natural oil-based polyols produced consistently have a higher hydroxyl content. A catalytic amount of fluoboric acid is used in this reaction. This amount should be below about 0.5% by weight of the entire reaction mixture or about 1.25% by weight of the amount of epoxidized oil used. Usually, the amount of fluoboric acid is between about 0.1% and 0.5% by weight of the total reaction mixture, and preferably, it is between about 0.3% and 0.5% by weight of the entire reaction mixture.

Examples of alcohols or alcohol mixtures that may be used in the hydroxylation reaction include, but are not limited to, monoalcohols such as methanol, ethanol, propanol, isopropanol and butanol. It is desirable to use at least some methanol in the hydroxylation reaction because it is the most reactive alcohol. Methanol may be used with solvents other than alcohols, such as chloroform, toluene, formic acid, or acetic acid. It is important during the hydroxylation step to always have an excess amount of alcohol present so as to prevent polymerization and the formation of products having higher viscosities.

Water is also an important component in this reaction. It reacts with the epoxy groups of the epoxidized natural oils to form two hydroxyl groups per epoxy group in some locations so as to increase the hydroxyl content of the natural oil-based polyols. Specifically, water contributes to about 10% or lower to dihydroxylation of the natural oil. Still further, it acts as a diluent to the fluoboric acid so that the acid is not reactive towards undesired cleavage of the triglyceride linkages present in the natural oil molecules. About 10 wt % to 30 wt % water should be used in this reaction. In the method of the present invention, the OH content of the polyol can be more precisely controlled than previous methods by varying the amount of water used in the reaction.

The mixture of alcohol and water is crucial in this reaction. The ratio of alcohol to water defines the polarity of the reaction media and limits the solubility of the epoxidized natural oil and the polyol in the reaction mixture. One phase is an alcohol/water mixture with a dissolved part of epoxidized natural oil and a dissolved part of newly formed polyol. The rest of the epoxidized natural oil is separated as undissolved droplets, the same as the undissolved part of the newly formed polyol. The reaction effectively takes place between dissolved epoxidized natural oil and alcohol/water. The reaction also takes place on the surface of the epoxidized natural oil droplets. In both cases, the molar ratio of alcohol/water to epoxy groups is many times higher than the stoichiometric ratio of alcohol/water to epoxidized natural oil, which strongly promotes the main reaction between alcohol and epoxy groups and diminishes undesirable side-reactions.

The molar ratio of alcohol to water should be between about 2:1 and 9:1. Preferably, the ratio of alcohol to water is between about 3:1 and 5:1. Preferably, this mixture is a water/methanol, water/isopropanol, or water/ethanol mixture. Most preferably, it is a water/methanol mixture. When methanol is the alcohol used, the polyol obtained has the best balance between OH number and viscosity. Polyols with higher OH numbers can be created with isopropanol/water mixtures, but these polyols also have higher viscosities. The hydroxylation reaction takes place at approximately the boiling temperature of the water/alcohol mixture.

Another benefit of the reaction taking place in a heterogeneous reaction system is the lower solubility of the polyol in the alcohol/water mixture. According to data in Table 1, shown below, the solubility of the newly-formed polyol decreases strongly with increasing water content in the mixture. In fact, when the amount of water present is between 10–30 wt %, the solubility of the polyol is decreased from 100% to 7.5%, which decreases the possibility of reaction between the epoxidized natural oil and the newly-formed polyol and suppresses the formation of high molecular weight molecules.

TABLE 1

Effect of the water content on solubility of epoxidized soybean oil and soy polyol in the methanol/water reaction mixture at the boiling temperature (64° C.)

| Water content in the methanol/ water mixture, (% by weight) | ESBO solubility in the methanol/ water mixture, (g/100 g of the mixture) | Polyol solubility in the methanol/water, (g/100 g of the mixture) | OH number |
| --- | --- | --- | --- |
| 0 | 65 | Unlimited | 186 |
| 3 | 16.9 | Unlimited | 187 |
| 6 | 9.7 | Unlimited | 188 |
| 10 | 6.2 | Unlimited | 196 |
| 15 | 2.9 | 26.4 | 201 |
| 20 | 2.3 | 16.6 | 207 |
| 30 | 1.4 | 7.5 | 193 |
| 40 | 0.8 | 3.5 | 143 |
| 60 | 0.9 | 2.6 | 149 |
| 80 | 0.5 | 2.3 | NA |
| 100 | 0.2 | 0.8 | NA |

Water also reacts with epoxy groups giving vicinal diols and increasing the OH number of the polyol. By regulating the alcohol to water ratio, it is possible to regulate the OH number of the polyol and find the best balance between the desirable OH number and viscosity. However, larger amounts of water decrease the reaction rate and thus require a larger amount of catalyst. A higher catalyst concentration promotes undesirable side-reactions such as hydrolysis, transesterification and crosslinking giving products of higher viscosity and lower OH number. Therefore, the alcohol to water ratio should be in certain limits, namely between 2:1 and 9:1, giving the preferable concentration of the dissolved epoxidized natural oil in the reaction mixture. At that concentration of dissolved epoxidized natural oil, the conversion of epoxy groups is the fastest, and undesirable reactions are minimal. Accordingly, the OH number of the polyol is the highest. Table 1 shows the effect of methanol/water ratio on the solubility of epoxidized soybean oil and soy polyols at the boiling temperature of the methanol (64° C.) and on the OH number and viscosity of the synthesized polyols.

Subsequent to the hydroxylation reaction, a neutralizing agent should be added to neutralize the fluoboric acid catalyst. Neutralizing agents that may be used include, but are not limited to, weak bases, metal bicarbonates, or ion-exchange resins. Preferably, the neutralizing agents are weakly-basic anionic ion-exchange resins. Examples of suitable neutralizing agents include, but are not limited to, ammonia, ammonia/water solution, calcium carbonate, sodium bicarbonate, magnesium carbonate, amines, and/or anionic ion-exchange resins.

The polyols made by the method of the present invention have a viscosity in the range of 1.0–7.0 Pa.s at room temperature. The viscosity of these polyols is lower than polyols made by other methods because the method of the present invention avoids substantial side-reactions, such as polymerization or crosslinking. Still further, the natural oil-based polyols made by the method of the present invention have a hydroxyl content ranging from 110 to 213 mg KOH/g. Preferably, the polyol has a high hydroxyl content which equals approximately one hydroxyl group per double bond of the natural oil. Natural oil-based polyols can be made in yields of 85–95% using any of the various embodiments of the process of the present invention.

By making polyols in a boiling reaction mixture, epoxidized natural oil is converted to polyols very quickly. The method of the present invention gives a low level of side reactions such as polymerization, cyclization, esterification, and crosslinking so as to produce polyols of narrow Molecular Weight Distribution (MWD). In fact, transesterification and diglyceride formation is negligible in this process.

This method for making natural oil-based polyols is illustrated in the following examples. These examples are not meant in any way to limit the scope of this invention.

EXAMPLE 1

A soy polyol was prepared from Flexol® epoxidized vegetable oil from Union Carbide. The epoxidized vegetable oil had an epoxide content of 7.1%, an iodine number of 1.0, an acid number of 0.2 mg KOH/g, a hydroxyl value of 5, a viscosity of 188 cST at 100° F., specific gravity of 0.992, and platinum-cobalt color of 61. The polyol was synthesized in a 500-mL three-necked round bottomed flask equipped with a reflux condenser. 126 g of methanol, 14.5 g of water, and 1.04 g of 48% $HBF_4$ (0.2% wt. of the pure acid in the total reaction mixture) catalyst were added into the flask. The mixture was heated to the boiling point of the alcohol, and epoxidized soybean oil (ESBO) (100 g) was then quickly added from an addition funnel. The reaction was continued for another 25 minutes for a total of 30 minutes. The reaction mixture was transferred into a plastic container and about $CaCO_3$ (10 g) powder was added as the neutralizing agent for the catalyst. The container was shaken for several minutes and then left standing for about one hour. The precipitate was filtered off. The excess water and alcohol were removed by vacuum distillation; for 30 minutes each was carried out by a water aspirator pump and by an oil vacuum pump. The product was found to have a hydroxyl value of 197 mg KOH/g and a viscosity of 7.8 Pa.s at 25° C.

EXAMPLE 2

A soy polyol was created from Flexol® epoxidized vegetable oil from Union Carbide. The epoxidized vegetable oil had an epoxide content of 7.1%, an iodine number of 1.0, an acid number of 0.2 mg KOH/g, a hydroxyl value of 5, a viscosity of 188 cST at 100° F., specific gravity of 0.992, and platinum-cobalt color of 61. The polyol was synthesized in a 500-mL three-round bottom necked RB flask equipped with a reflux condenser. 126 g of methanol, 14.5 g of water, and 2.08 g of 48% $HBF_4$ (0.4% wt. of the pure acid in the total reaction mixture) catalyst were added into the flask. The mixture was heated to the boiling point of the alcohol, and ESBO (100 g) was then quickly added from an addition funnel. The reaction was continued for another 25 minutes for a total of 30 minutes. The reaction mixture was transferred into a plastic container, and ion-exchange resin (10 g) (Lewatitte MP-64 from Bayer) was added as the neutralizing agent for the catalyst. The container was shaken for about one hour. The solid was then filtered off. The excess water and alcohol were removed by vacuum distillation; for 30 minutes each was carried out by a water aspirator pump and by an oil vacuum pump. The product was found to have a hydroxyl value of 196 mg KOH/g and a viscosity of 8.2 Pa.s at 25 ° C.

EXAMPLE 3

A soy polyol was created from Flexol® epoxidized vegetable oil from Union Carbide. The polyol was synthesized in a 500-mL three-necked RB flask equipped with a reflux condenser. 112.5 g of methanol, 12.5 g of water and 2.08 g of 48% $HBF_4$ (0.4% wt. of the pure acid in the total reaction mixture) catalyst were added into the flask. The mixture was heated to the boiling point of the alcohol, and ESBO (100 g) was then quickly added from an addition funnel. The reaction was continued for another 25 minutes for a total of 30 minutes. The reaction mixture was transferred into a plastic container, and $CaCO_3$ (10 g) powder were added as the catalyst neutralizing agent. The container was shaken for a few minutes and left standing for about one hour. The precipitate was filtered off. The excess water and alcohol were removed by vacuum distillation; for 30 minutes each was carried out by a water aspirator pump and by an oil vacuum pump. The product was found to have a hydroxyl value of 205 and a viscosity of 7.8 Pa.s at 25° C.

EXAMPLE 4

A soy polyol was created from Flexol® epoxidized vegetable oil from Union Carbide. The polyol was synthesized in a 500-mL three-necked RB flask equipped with a reflux condenser. 101 g of methanol, 25 g of water, and 2.08 g of 48% $HBF_4$ (0.4% wt. of the pure acid in the total reaction mixture) catalyst were added into the flask. The mixture was heated to the boiling point of the alcohol, and ESBO (100 g) was then quickly added from an addition funnel. The reaction was continued for another 25 minutes for a total time of 30 minutes. The reaction mixture was transferred into a plastic container, and powdered CaCO$_3$ (10 g) was added as the catalyst neutralizing agent. The container was shaken for a few minutes and then left standing for about one hour. The deposit was filtered off. The excess water and alcohol were removed by vacuum distillation; for 30 minutes each was carried out by a water aspirator pump and by an oil vacuum pump. The product was found to have a hydroxyl value of 207 and a viscosity of 11.8 Pa.s at 25 °C.

EXAMPLE 5

A soy polyol was created from Flexol® epoxidized vegetable oil from Union Carbide. The polyol was synthesized in a 2000-mL three-necked RB flask equipped with a reflux condenser. 400 g of methanol, 100 g of water, and 3.6 g of 48% HBF$_4$ (0.35% wt. of the pure acid in the total reaction mixture) catalyst were added into the flask. The mixture was heated to the boiling point of the alcohol, and ESBO (400 g) was then quickly added from an addition funnel. The reaction was continued for another 25 minutes for a total of 30 minutes. The reaction mixture was transferred into a plastic container, and ion-exchange resin (40 g) (Lewatitte MP-64 from Bayer) was added as the neutralizing agent for the catalyst. The container was shaken for about one hour. The solid was filtered off. The excess water and alcohol were removed by vacuum distillation; for 30 minutes each was carried out by a water aspirator pump and by an oil vacuum pump. The product was found to have a hydroxyl value of 212 and a viscosity of 10.1 Pa.s at 25° C.

EXAMPLE 6

A soy polyol was created from PLAS-CHEK® epoxidized vegetable oil from Ferro Corporation. The epoxidized vegetable oil had an epoxide content of 6.8%, an iodine number of 1.2, an acid number of 0.3 mg KOH/g, viscosity of 138 cST at 100° F., specific gravity of 0.990, and APHA color of 140. The polyol was synthesized in a 2000 mL three-necked RB flask equipped with a reflux condenser. 400 g of methanol, 100 g of water, and 3.6 g of 48% HBF$_4$ (0.35% wt. of the pure acid in the total reaction mixture) catalyst were added into the flask. The mixture was heated to the boiling point of the alcohol, and ESBO (400 g) was then quickly added from an addition funnel. The reaction was continued for another 25 minutes for a total of 30 minutes. The reaction mixture was transferred into a plastic container and ion-exchange resin (40 g) (Lewatitte MP-64 from Bayer) were added as the neutralizing agent for the catalyst. The container was shaken for about one hour. The solid was filtered off. The excess water and alcohol were removed by vacuum distillation; for 30 minutes each was carried out by a water aspirator pump and by an oil vacuum pump. The product was found to have a hydroxyl value of 207 and a viscosity of 10.8 Pa.s at 25° C.

EXAMPLE 7

A soy polyol was created from PLAS-CHEK® epoxidized vegetable oil from Ferro Corporation. The polyol was synthesized in a 2000-mL three-necked RB flask equipped with a reflux condenser. 400 g of methanol, 100 g of water, and 3.6 g of 48% HBF$_4$ (0.35% wt. of the pure acid in the total reaction mixture) catalyst were added into the flask. The mixture was heated to the boiling point of the alcohol, and ESBO (400 g) was then quickly added from an addition funnel. The reaction was continued for another 25 minutes for a total of 30 minutes. The reaction mixture was transferred into a plastic container, and powdered CaCO$_3$ (20 g) was added as the catalyst neutralizing agent. The container was shaken for a few minutes and then left standing for about one hour. The deposit was filtered off. The excess water and alcohol were removed by vacuum distillation; for 30 minutes each was carried out by a water aspirator pump and by an oil vacuum pump. The product was found to have a hydroxyl value of 208 and a viscosity of 10.6 Pa.s at 25° C.

EXAMPLE 8

A soy polyol was created from PLAS-CHEK® epoxidized vegetable oil from Ferro Corporation. The polyol was synthesized in a 500-mL three-necked RB flask equipped with a reflux condenser. 116 g of isopropanol, 5.8 g of water and 1.8 g of 48% HBF$_4$ (0.5% wt. of the pure acid in the total reaction mixture) catalyst were added into the flask. The mixture was heated to the boiling point of the alcohol, and ESBO (50 g) was then quickly added from an addition funnel. The reaction was continued for another 25 minutes for a total of 30 minutes. The reaction mixture was transferred into a plastic container, and powdered CaCO$_3$ (5 g) was added as the catalyst neutralizing agent. The container was shaken for a few minutes and then left standing for about one hour. The deposit was filtered off. The excess water and alcohol were removed by vacuum distillation; for 30 minutes each was carried out by a water aspirator pump and by an oil vacuum pump. The product was found to have hydroxyl value of 207 and a viscosity of 25 Pa.s at 25° C.

EXAMPLE 9

A soy polyol was created from PLAS-CHEK® epoxidized vegetable oil from Ferro Corporation. The polyol was synthesized in a 1000-mL three-necked RB flask equipped with a reflux condenser. 300 g of isopropanol, 100 g of water, and 4.2 g of 48% HBF$_4$ (0.5% wt. of the pure acid in the total reaction mixture) catalyst were added into the flask. The mixture was heated to the boiling point of the alcohol, and ESBO (100 g) was then quickly added from an addition funnel. The reaction was continued for another 25 minutes for a total of 30 minutes. The reaction mixture was transferred into a plastic container and powdered CaCO$_3$ (10 g) was added as the catalyst neutralizing agent. The container was shaken for a few minutes and then left standing for about one hour. The deposit was then filtered off. The excess water and alcohol were removed by vacuum distillation; for 30 minutes each was carried out by a water aspirator pump and by an oil vacuum pump. The product was found to have a hydroxyl value of 252 and a viscosity of 32 Pa.s at 25° C.

EXAMPLE 10

A soy polyol was created from PLAS-CHEK® epoxidized vegetable oil from Ferro Corporation. The polyol was synthesized in a 500-mL three-necked RB flask equipped with a reflux condenser. 113 g of ethanol, 5.7 g of water and 0.5 g of 48% HBF$_4$ (0.1% wt. of the pure acid in the total reaction mixture) catalyst were added into the flask. The mixture was heated to the boiling point of alcohol, and ESBO (50 g) was then quickly added from an addition funnel. The reaction was continued for another 25 minutes for a total of 30 minutes. The reaction mixture was transferred into a plastic container, and powdered CaCO$_3$ (5 g) was added as the catalyst neutralizing agent. The container was shaken for a few minutes and then left standing for about one hour. The deposit was then filtered off. The excess water and alcohol were removed by vacuum distillation; for 30 minutes each was carried out by a water aspirator pump and by an oil vacuum pump. The product was found to have a hydroxyl value of 187 and a viscosity of 8 Pa.s at 25° C.

In another embodiment of the present invention, the natural oil-based polyols created by the method of the present invention or by other methods may be reacted with isocyanates to form polyurethanes. The natural oil-based polyols produced by the present invention have a range of hydroxyl content varying from 110 to 213 mg KOH/g, which will lead to polyurethane materials having a range of physical and mechanical properties, suitable for a variety of applications.

Alternatively, a filler may be added to the natural oil-based polyol before it is reacted with the isocyanate. Examples of fillers that may be added include, but are not limited to, silica, alumina, calcium carbonate, dolomite, silicates, glass, ceramic, sand, clay, and talc. The filler may be combined with the natural oil-based polyol in about 1 to 200% by weight of the natural oil-based polyol. High modulus fillers such as silica and alumina may be abrasive if applied with machines requiring pumping, but they impart high electrical properties and excellent mechanical properties. Soft fillers like calcium carbonate give excellent flow properties and are more suitable for machine application. Using large quantities of fillers improves the thermal conductivity of the products created so that excellent dielectric strength may be provided.

One of the problems with using urethanes for electrical insulation is caused by the reaction of isocyanates with water, resulting in carbon dioxide gas formation and foaming. However, new moisture scavengers have been developed which react with water before it reacts with the isocyanate, allowing polyurethanes to be used in the electrical insulation field. Conventional moisture scavengers may be used in making the polyurethanes of the present invention.

In forming the polyurethane, the isocyanate reacts with the hydroxyl groups of the natural oil-based polyol. The natural oil-based polyol and the isocyanate are combined in approximately stoichiometric quantities. It is acceptable to use up to about 10% in excess of the stoichiometric quantity of either of these components. Examples of isocyanates that can be used include, but are not limited to, polymeric or crude diphenylmethane diisocyanate (MDI), modified MDI including hydrogenated MDI (HMDI), isophorone diisocyanate, and 2,4-toluene diisocyanate (TDI). PAPI 2901, available from Dow Chemicals, Midland, Mich. 48674, is an example of a polymeric or crude MDI that may be used. Isonate 2143 L, available from Dow Chemicals, is an example of a non-polymeric MDI that may be used. HMDI is a hydrogenated MDI, which is non-aromatic and can be used where light stability, arc and tracking resistance are required. The selection of the isocyanate component affects the crosslinking of the polyurethane.

Still further, a drying agent or an anti-foaming agent may be added to the polyurethane, as desired. A drying agent is recommended because polyurethanes are very sensitive to moisture. An example of a drying agent that may be used is a zeolite paste such as Baylith L Paste, which is comprised of a 50% dispersion of zeolite in castor oil and may be obtained from Bayer Corp., 100 Bayer Road, Pittsburgh, Pa. 15205. In fact, a zeolite drying agent is the most preferred drying agent for polyurethane reactions. Additives such as pigments may also be added in forming the polyurethane.

The polyol and the filler should both be dried before being mixed together. The polyol, the filler and the other optional additives should then be mixed while the polyol and the filler are still hot so as to form a polyol component. The polyol component is mixed under vacuum conditions at about 40–60° C. for about 5 minutes or until foaming stops. This removes trapped air. Next, an approximately stoichiometric amount of an isocyanate is added. The isocyanate is stirred with the polyol component under nitrogen for about 2 minutes and then under vacuum for about 5 minutes at about 60° C. until foaming stops. The mixture of the polyol with the isocyanate can be poured into a mold under nitrogen and then heated at about 110° C. for about 24 hours to complete the reaction.

The polyurethane resins of the present invention can be cured at room temperature, although higher temperatures accelerate the curing process thus avoiding the use of a catalyst. At higher curing temperatures, the viscosity of the polyurethane is reduced and thus, gas evacuation from the compound is facilitated. This gives a higher degree of curing, which results in a final product having a higher glass transition point.

Polyurethane compounds based on natural oil-based polyols have higher thermal stability both in air and nitrogen than corresponding polyurethane compounds based on polypropylene oxide (PPO) polyols, which are sometimes used in electroinsulation. Natural oil-based urethane compounds have better hydrolytic stability and lower absorption of water than corresponding PPO-based compounds. Still further, natural oil-based polyurethane compounds have several orders higher bulk and surface resistivity than amine or anhydride cured epoxy resins.

Polyurethane casting resins based on natural oil-based polyols are relatively low viscosity systems. Thus, they are suitable for impregnation of electrocoils, and when filled, they are useful as casting insulators, dry transformers, and other various electrical components, which is another embodiment of the present invention. Polyurethanes made from natural oil-based polyols can be cast into various electrical components by pouring the polyol and isocyanate mixture into a mold. Typically, these compounds are used in mid-voltage insulating applications (up to 35 kV), such as cable connectors and dry transformers as well as in the electronic industry for encapsulation, potting, embedding and casting. The products formed with polyurethane made from natural oil-based polyols can be rigid or elastic depending on customer needs. These products may also be used in non-electrical applications where excellent mechanical and chemical properties as well as machinability, hydrophobicity, colorability and economy are factors. Additional factors that make these products useful for a variety of applications are the fact that they are easy to process even at low temperatures and the fact that the hardness of the products created can be varied by changing component ratios.

The appearance of the polyurethane materials created from natural oil-based polyols ranges from rigid plastics to soft rubber at room temperature. These polyurethanes have excellent electrical properties. Polyurethanes made from soybean oil and safflower oil polyols are more rigid, have better mechanical and electrical properties, and have better thermal resistance because of their higher transition temperature than polyurethanes made from other natural oil-based polyols. Specifically, they have higher strength and lower dielectric permittivity and loss factor at room temperature because of their higher glass transition temperature. Still further, polyurethanes made from soy and safflower polyols have more crosslinking and thus are denser than polyurethanes made from other natural oil-based polyols. The addition of a filler improves both mechanical strength and dielectric strength of all these polyurethanes made from natural oil-based polyols. Various mechanical and electrical properties of polyurethanes made from soybean oil-based polyols that contain varying amounts of filler are shown in the following table:

The mixture is then poured into a mold under nitrogen and the unit is left under vacuum to evacuate bubbles (5 minutes at 60° C.) and then the vacuum is removed. The sample is

TABLE 2

| SiO$_2$ | TRANSITION TEMP., Tg, ° C. | | PERMITTIVITY | $\epsilon''/\epsilon'$ | SURFACE RESISTIVITY | VOLUME RESISITIVITY | AVERAGE DIELECTRIC STRENGTH |
|---|---|---|---|---|---|---|---|
| | DMTA | TMA | $\epsilon'$ | tan δ | ohm | ohm · cm | KV/mm |
| 0 (Isonate) | 66 | 55 | 3.1 | 0.004 | 5.37E+15 | 1.69E+16 | 19.5 |
| 150 (Isonate) | 75 | 63 | 3.49 | 0.003 | 1.98E+15 | 9.41E+15 | 19.7 |
| 200 (Isonate) | 73 | 68 | — | — | — | — | — |
| 0 (PAPI) | 67 | 62 | 3.18 | 0.005 | 5.37E+15 | 1.72E+16 | 17.8 |
| 150 (PAPI) | 74 | 66 | 3.5 | 0.003 | 1.98E+15 | 1.73E+16 | 20.6 |
| 200 (PAPI) | 80 | 63 | 3.61 | 0.0029 | 1.98E+15 | 9.26E+15 | 19.7 |

The following are examples of polyurethanes that may be created using natural oil-based polyols without using a filler. These examples have not been conducted. These examples are not meant in any way to limit the scope of this invention.

EXAMPLE 11

A cast polyurethane resin is made using 60 parts of soy polyol, the product of Example 1, 29 parts of Isonate 2143L, and 0.6 parts of anti-foaming agent. The soy polyol and the antifoaming agent are mixed together to form a polyol component. This polyol component is dried for 20 hours at 110° C. Next, Isonate 2143L is added at 60° C. The polyol and the isocyanate components are stirred under nitrogen for two minutes and then under vacuum for five minutes at 60° C. until the foaming stops. The mixture is then poured into a mold under nitrogen and the unit is left under vacuum to evacuate bubbles (5 minutes at 60° C.) and then the vacuum is removed. The sample is baked for 24 hours at 110° C. to complete the reaction. The sample is then cooled to room temperature and demolded. The cast resin may be molded into electroinsulating components.

EXAMPLE 12

A cast polyurethane resin is made using 40 parts of soy polyol, the product of Example 2, and 23 parts of Isonate 2143L without using any drying agent, antifoaming agent, or filler. The polyol is dried for 20 hours at 110° C. Next, Isonate 2143L is added at 60° C. The polyol and the isocyanate components are stirred under nitrogen for two minutes and then under vacuum for five minutes at 60° C. until the foaming stops. The mixture is then poured into a mold under nitrogen and the unit is left under vacuum to evacuate bubbles (5 minutes at 60° C.) and then the vacuum is removed. The sample is baked for 24 hours at 110° C. to complete the reaction. The sample is then cooled to room temperature and demolded. The cast resin may be molded into electroinsulating components.

EXAMPLE 13

A cast polyurethane resin is made from 60 parts of soy polyol, the product of Example 3, 27 parts of PAPI 2901, 3 parts of drying agent, and 0.6 parts antifoaming agent. The soy polyol, the drying agent and the antifoaming agent are mixed together to form a polyol component. This polyol component is dried for 20 hours at 110° C. Next, PAPI 2901 is added at 60° C. The polyol and the isocyanate components are stirred under nitrogen for two minutes and then under vacuum for five minutes at 60° C. until the foaming stops.

baked for 24 hours at 110° C. to complete the reaction. The sample is then cooled to room temperature and demolded. The cast resin may be molded into electroinsulating components.

EXAMPLE 14

A cast polyurethane resin is created using 20 parts of soy polyol, the product of Example 4, and 9.4 parts of Isonate 2143L without using any drying agent, antifoaming agent, or filler, using the same procedures as illustrated in Example 12. The cast resin may be molded into electroinsulating components.

EXAMPLE 15

A cast polyurethane resin is created using 20 parts of soy polyol, the product of Example 5, and 8.4 parts of Isonate 2143L without using any drying agent, antifoaming agent, or filler, using the same procedures as illustrated in Example 12. The cast resin may be molded into electroinsulating components.

EXAMPLE 16

A cast polyurethane resin is created using 20 parts of soy polyol, the product of Example 6, and 7.6 parts of Isonate 2143L without using any drying agent, antifoaming agent, or filler, using the same procedures used were the same as illustrated in Example 12. The cast resin may be molded into electroinsulating components.

EXAMPLE 17

A cast polyurethane resin is created using 20 parts of soy polyol, the product of Example 7, and 7.4 parts of Isonate 2143L without using any drying agent, antifoaming agent, or filler, using the same procedures as illustrated in Example 12. The cast resin may be molded into electroinsulating components.

EXAMPLE 18

A cast polyurethane resin is created using 20 parts of soy polyol, the product of Example 8, and 7.2 parts of Isonate 2143L without using any drying agent, antifoaming agent, or filler, using the same procedures as illustrated in Example 12. The cast resin may be molded into electroinsulating components.

EXAMPLE 19

A cast polyurethane resin is created using 20 parts of soy polyol, the product of Example 9, and 5.8 parts of Isonate 2143L without using any drying agent, antifoaming agent, or filler, using the same procedures as illustrated in Example 12. The cast resin may be molded into electroinsulating components.

The following are examples of polyurethane materials that may be created using the aforementioned natural oil-based polyols by using a filler. These examples have not been conducted. These examples are not meant in anyway to limit the scope of this invention.

EXAMPLE 20

A cast polyurethane resin containing silica filler is made from 40 parts of soy polyol, the product of Example 1,20 parts of isonate 2143L, 2 parts of drying agent, 0.4 parts of antifoaming agent, and 60 parts of silica filler. Silica having an average particle size of 6.5 microns is used.

The silica is dried for 20 hours at 110° C. The soy polyol, drying agent and antifoaming agent are mixed together to form a polyol component. This polyol component is dried for 20 hours at 110° C. The polyol component is mixed with the silica while still hot. These components are stirred for 2 minutes and then placed under vacuum at 60° C. for 5 minutes until foaming stops. Next, Isonate 2143L is added at 60° C. The polyol and the isocyanate components are stirred under nitrogen for 2 minutes and then under vacuum for 5 minutes at 60° C. until the foaming stops. The mixture is then poured into a mold under nitrogen and the unit is left under vacuum to evacuate bubbles (5 minutes at 60° C.) and then the vacuum is removed. The sample is baked for 24 hours at 110° C. to complete the reaction. The sample is then cooled to room temperature and demolded. The cast resin may be molded into electroinsulating components.

EXAMPLE 21

A cast polyurethane resin containing silica filler is made with 40 parts of soy polyol, the product of Example 2, 18 parts of PAPI 2901, 2 parts of drying agent, 0.4 parts of antifoaming agent, and 80 parts of silica filler.

The silica is dried for 20 hours at 110° C. The soy polyol, drying agent and antifoaming agent are mixed together to form a polyol component. This polyol component is dried for 20 hours at 110° C. The polyol component is mixed with the silica while still hot. These components are stirred for 2 minutes and then placed under vacuum at 60° C. for 5 minutes until foaming stops. Next, PAPI 2901 is added at 60° C. The polyol and the isocyanate components are stirred under nitrogen for 2 minutes and then under vacuum for 5 minutes at 60° C. until the foaming stops. The mixture is then poured into a mold under nitrogen and the unit is left under vacuum to evacuate bubbles (5 minutes at 60° C.) and then the vacuum is removed. The sample is baked for 24 hours at 110° C. to complete the reaction. The sample is then cooled to room temperature and demolded. The cast resin may be molded into electroinsulating components.

From the foregoing, it will be seen that this invention is one well adapted to attain all the ends and objects hereinabove set forth together with other advantages which are obvious and inherent to the structure. It will be understood that certain features and subcombinations are of utility and may be employed without reference to other features and subcombinations. This is contemplated by and is within the scope of the claims. Since many possible embodiments may be made of the invention without departing from the scope thereof, it is to be understood that all matter herein set forth is to be interpreted as illustrative and not in a limiting sense.

We claim:

1. A method for making a natural oil-based polyol from natural oil, comprising:
    (a) adding a peroxyacid to natural oil wherein said peroxyacid and said natural oil react to form an epoxidized natural oil; and
    (b) adding said epoxidized natural oil directly from step (a) without intermediate purification to a mixture of an alcohol, water, and a catalytic amount of fluoboric acid wherein said water is about 10% to 30% by weight of all the components and wherein said epoxidized natural oil reacts with said mixture to form a natural oil-based polyol.

2. The method of claim 1, wherein said alcohol is methanol, ethanol, or isopropanol.

3. The method of claim 1, wherein said peroxyacid is selected from the group consisting of m-chloroperbenzoic acid and peracetic acid.

4. The method of claim 1, wherein said peroxyacid is added to said natural oil in a dropwise fashion, said natural oil and said peroxyacid are stirred so as to react to form epoxidized natural oil, said epoxidized natural oil is added dropwise to said mixture, and said mixture and said epoxidized natural oil are stirred wherein a natural oil-based polyol forms.

5. The method of claim 1, wherein said peroxyacid is in a solvent, said epoxidized natural oil is formed in said solvent, and said epoxidized natural oil in said solvent is added to said mixture.

6. The method of claim 5, wherein said solvent is selected from the group consisting of acetic acid, formic acid, and chloroform.

7. The method of claim 1, wherein step (b) takes place at about the boiling temperature of said water and alcohol mixture.

8. The method of claim 1, wherein said catalytic amount of fluoboric acid is between about 0.1% and 0.5% by weight of all the components.

9. The method of claim 1, wherein said catalytic amount of fluoboric acid is about 1.25% by weight of the amount of epoxidized natural oil used.

10. A method of making a natural oil-based polyol from epoxidized natural oil, comprising:
    hydroxylating epoxidized natural oil with a catalytic amount of fluoboric acid, an alcohol, and water, wherein said water is about 10% to 30% by weight of all the components.

11. The method of claim 10, wherein said catalytic amount of fluoboric acid is between about 0.1% and 0.5% by weight of all the components.

12. The method of claim 10, wherein said epoxidized natural oil has about 2 to 6 epoxy groups per molecule.

13. The method of claim 10, wherein said alcohol is methanol, ethanol or isopropanol.

14. The method of claim 13, wherein the molar ratio of alcohol to water is between about 2:1 and 9:1.

* * * * *

UNITED STATES PATENT AND TRADEMARK OFFICE
CERTIFICATE OF CORRECTION

PATENT NO. : 6,433,121 B1                                    Page 1 of 1
DATED      : August 13, 2002
INVENTOR(S) : Petrovic et al.

It is certified that error appears in the above-identified patent and that said Letters Patent is hereby corrected as shown below:

Column 1,
Line 26, delete "A" between "," and "soybean".
Line 38, delete "of ten" and insert -- often --.

Column 11,
Table 2, column 1, delete "       and insert -- FILLER, %
                       SiO₂"              SiO₂    --.
Table 2, columns 2 and 3, delete "           and insert --    GLASS
                          TRANSITION                      TRANSITION
                          TEMP., Tg, ° C.                 TEMP., Tg, °C.

DMTA   TMA"                     DMTA   TMA --.

Signed and Sealed this

Fourth Day of February, 2003

JAMES E. ROGAN
*Director of the United States Patent and Trademark Office*